(12) United States Patent
Kamatani et al.

(10) Patent No.: US 8,946,501 B2
(45) Date of Patent: Feb. 3, 2015

(54) LIQUID LEAKAGE DETECTION SYSTEM

(75) Inventors: Naoyuki Kamatani, Chiba (JP); Tadashi Ishikawa, Tokyo (JP); Yoshiaki Hasebe, Tokyo (JP)

(73) Assignee: Aqua Power System, Japan, Tokyo (JP)

( * ) Notice: Subject to any disclaimer, the term of this patent is extended or adjusted under 35 U.S.C. 154(b) by 61 days.

(21) Appl. No.: 13/814,979

(22) PCT Filed: Aug. 13, 2010

(86) PCT No.: PCT/JP2010/063779
§ 371 (c)(1),
(2), (4) Date: Apr. 22, 2013

(87) PCT Pub. No.: WO2012/020507
PCT Pub. Date: Feb. 16, 2012

(65) Prior Publication Data
US 2013/0211329 A1      Aug. 15, 2013

(51) Int. Cl.
| | | |
|---|---|---|
| A61F 13/15 | (2006.01) |
| A61M 5/50 | (2006.01) |
| A61B 5/02 | (2006.01) |
| A61M 5/168 | (2006.01) |
| A61M 1/36 | (2006.01) |

(52) U.S. Cl.
CPC .......... *A61M 5/5086* (2013.01); *A61B 5/02042* (2013.01); *A61M 5/16831* (2013.01); *A61M 1/3653* (2013.01); *A61M 5/16836* (2013.01); *A61M 1/3656* (2014.02); *A61M 2205/15* (2013.01)
USPC ........... 604/361; 340/604; 340/605; 600/362; 600/371

(58) Field of Classification Search
CPC ..................... A61M 5/16831; A61M 5/16836; A61M 2001/3656; A61M 1/3653; A61M 2205/15; A61B 5/02042
USPC .................... 340/604; 600/309, 371; 604/361
See application file for complete search history.

(56) References Cited

U.S. PATENT DOCUMENTS

| 6,210,835 | B1 * | 4/2001 | Arai ........................ 429/231.95 |
| 2002/0137999 | A1 * | 9/2002 | Bandeian et al. ............. 600/371 |
| 2002/0198483 | A1 * | 12/2002 | Wariar et al. ................ 604/5.01 |
| 2003/0009131 | A1 * | 1/2003 | Van Antwerp et al. ........ 604/111 |
| 2003/0152815 | A1 * | 8/2003 | LaFollette et al. ................ 429/7 |
| 2004/0225255 | A1 * | 11/2004 | Ono ................................. 604/65 |
| 2007/0293748 | A1 * | 12/2007 | Engvall et al. ................ 600/371 |
| 2008/0077023 | A1 * | 3/2008 | Campbell et al. ............. 600/502 |
| 2008/0249487 | A1 * | 10/2008 | Engvall ........................ 604/307 |

(Continued)

FOREIGN PATENT DOCUMENTS

| JP | 2006-055588 | 3/2006 |
| JP | 3152998 | 8/2009 |

(Continued)

*Primary Examiner* — Nicholas Lucchesi
*Assistant Examiner* — Gerald Landry, II
(74) *Attorney, Agent, or Firm* — Clark & Brody (57) ABSTRACT

A liquid leakage detection system requiring no power supply from an outer source and configured to be relatively simple and moderate in price. A liquid leakage detection system (10) including an infusion tube (11), a syringe needle (12) coupled to the infusion tube (11), an absorbent element (16) adapted to be placed in the vicinity of a point (12*a*) of the syringe needle (12) to be pricked through a patient skin and a sensor unit (14) located on an upper side or within the absorbent element (16).

4 Claims, 10 Drawing Sheets

(56) References Cited

U.S. PATENT DOCUMENTS

| | | | |
|---|---|---|---|
| 2009/0082653 A1* | 3/2009 | Rohde | 600/347 |
| 2009/0088613 A1* | 4/2009 | Marttila et al. | 600/309 |
| 2009/0105627 A1* | 4/2009 | Rohde | 604/4.01 |
| 2009/0322543 A1* | 12/2009 | Crnkovich et al. | 340/604 |
| 2010/0102975 A1* | 4/2010 | Vossmeyer et al. | 340/636.19 |
| 2014/0200538 A1* | 7/2014 | Euliano et al. | 604/361 |

FOREIGN PATENT DOCUMENTS

| | | |
|---|---|---|
| JP | 2010-523197 | 7/2010 |
| WO | 2010/058796 | 5/2010 |

* cited by examiner

LIQUID LEAKAGE DETECTION SYSTEM

TECHNICAL FIELD

The present invention relates to liquid leakage detection systems and more particularly to liquid leakage detection systems for the medical purpose of detecting leakage of various kinds of liquid possibly occurring during drip infusion, blood collection, returning of blood from dialysis machine back to patient bodies, collection of various kinds of bodily fluids, for example, cerebrospinal fluid, ascitic fluid or pleural effusion or returning of such bodily fluids back to patient bodies.

BACKGROUND

Conventionally, a system used to detect leakage of liquid from a syringe needle having been pricked into a human body is well known. For example, JP 2006-55588 A (PTL 1) discloses a liquid leakage detection system including a circuit component formed on a copper-clad laminate, circuit terminals located on the circuit component and a sensor main body.

CITATION LIST

Patent Literature

{PTL 1}: JP 2006-55588 A

SUMMARY

Technical Problem

In the detection system disclosed in PTL 1, when the liquid such as blood flows between the circuit terminals of the circuit component which is in unelectrified open-circuit condition, the open circuit is changed to an electrified closed circuit whereupon the sensor main body is actuated to send out an alarm, thereby informing the persons in charge of a leakage from the needle is occurring.

However, in such detection system, it is required to include a power supply part since the circuit component must be always kept to be energized with weak voltage and, in addition, it is required to put the copper-clad laminate in contact with a patient body. Consequently, the patient might feel uncomfortable during use of the detection system.

An object of the present invention is to improve the liquid leakage detection system of prior art, thereby providing a liquid leakage detection system requiring no power supply from an outer source and having an arrangement which is more moderate in price and more simple than the system of prior art.

Solution to Problem

According to the present invention, there is provided a liquid leakage detection system including an infusion tube, a syringe needle coupled to the infusion tube, an absorbent element adapted to be placed in a vicinity of a point of the syringe needle to be pricked through a patient skin and a sensor unit located on an upper side or within the absorbent element.

According to one embodiment of the present invention, the sensor unit is composed of a liquid battery adapted to generate electricity in the presence of the leaked liquid.

According to another embodiment of the present invention, the sensor unit is composed of the liquid battery and a sender coupled to the liquid battery.

According to even another embodiment of the present invention, the sensor unit is provided to the absorbent element by means of a pressure-sensitive adhesive fixing tape.

According to still another embodiment of the present invention, the liquid battery includes a positive electrode plate, a negative electrode plate, positive-electrode active material directly or indirectly in contact with both the positive electrode plate and the negative electrode plate, and an external capsule sheet adapted to capsule them and wherein an electrical insulator layer is interposed between the positive electrode plate and the negative electrode plate.

According to yet another embodiment of the present invention, the absorbent element is interposed between the inner surface of the external capsule sheet and the liquid battery so that the positive electrode plate and the negative electrode plate may be wrapped with the absorbent element within the external capsule sheet.

Advantageous Effects of Invention

With the liquid leakage detection system according to the present invention, the liquid leakage can be detected by the relatively compact sensor unit adapted to generate electricity in response to leakage of the liquid without power supply from an outside source. In this way, the liquid leakage can be quickly detected with use of the arrangement which is more moderate in price and more simple than conventional liquid leakage detection devices and systems using the electronic circuits and the semiconductor elements.

DESCRIPTION OF EMBODIMENTS

Figure 1:
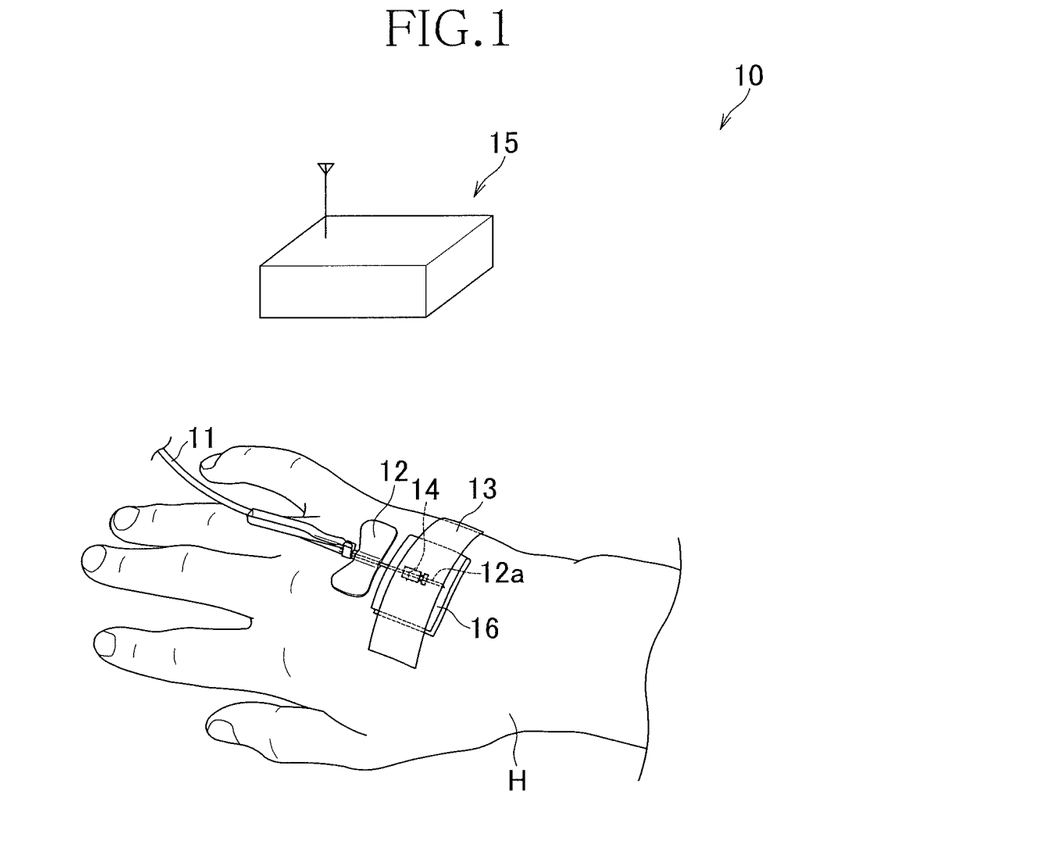
FIG. 1 is a perspective view of a liquid leakage detection system.
Figure 2:
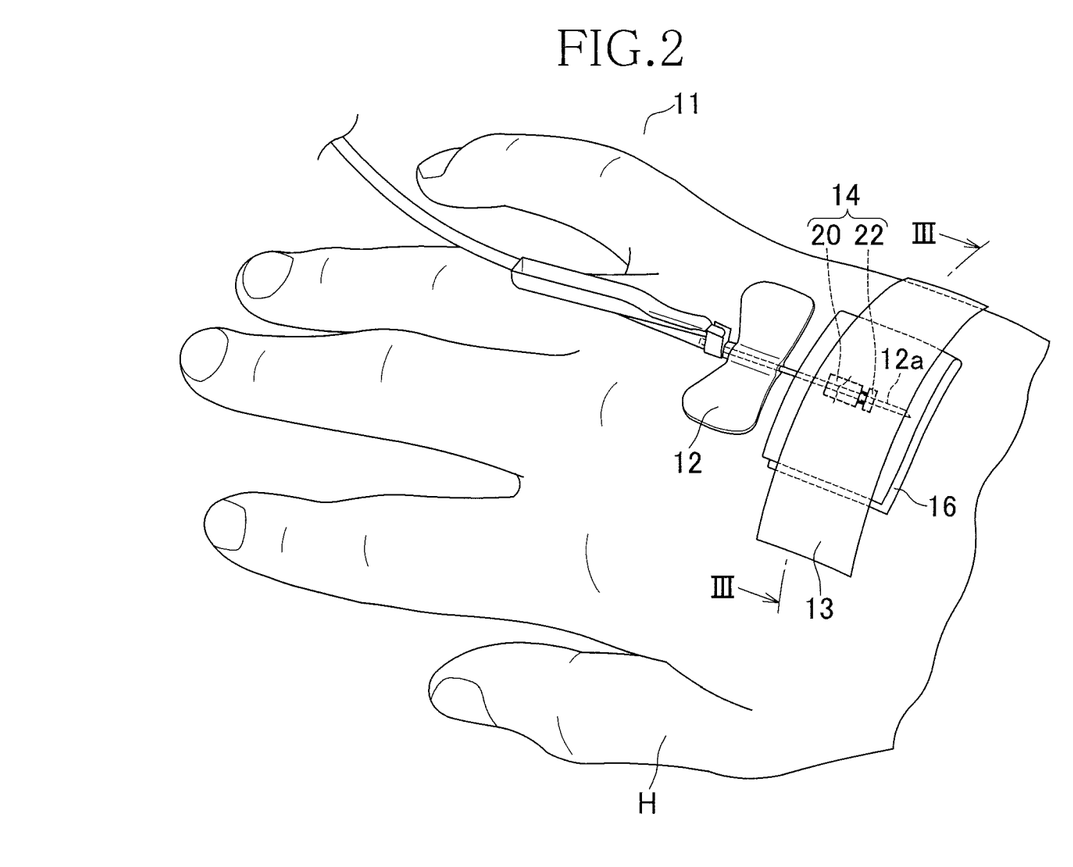
FIG. 2 is a partially scale-enlarged perspective view of the liquid leakage detection system.

Referring to FIGS. 1 and 2, a liquid leakage detection system 10 includes an infusion tube 11 coupled to a bag for drip infusion or a bag for blood collection, a butterfly needle (syringe needle) 12 coupled to the tube 11 and to be pricked into blood vessel on top H of a patient hand, a sensor unit 14 fixed to the patient hand by a pressure-sensitive adhesive fixing tape 13, and a receiver 15 to receive electrical waves emitted from the sensor unit 14. Between the pressure-sensitive adhesive fixing tape 13 and the vicinity of a point 12a of the butterfly needle 12 pricked into the blood vessel, an absorbent element 16, for example, folded gauze for blood stanching is interposed. As used herein, the term "liquid" means various kinds of liquids used for transfusion in a medical front, for example, blood, drip infusion liquid, cerebrospinal fluid, ascitic fluid or pleural effusion.

Figure 3:
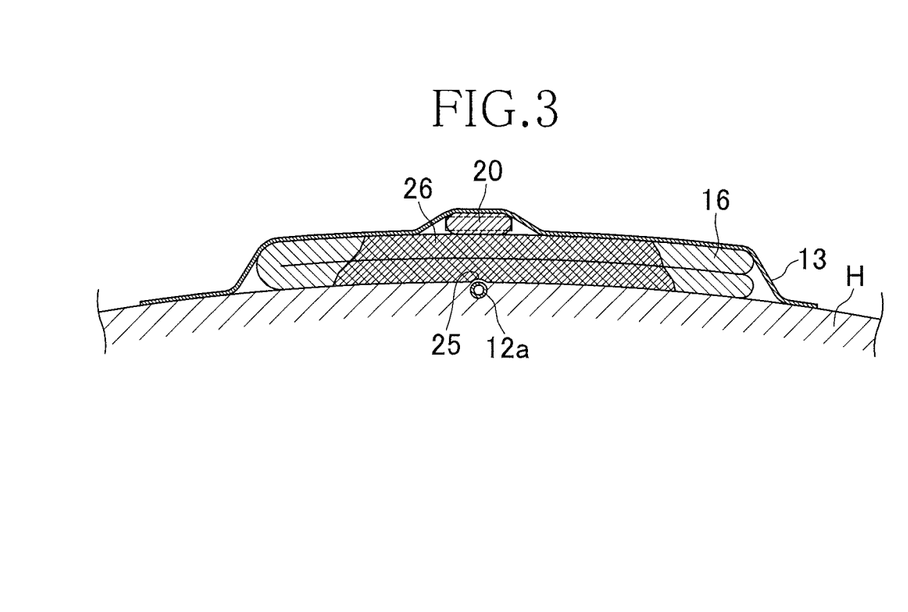
FIG. 3 is a sectional view taken along line III-III in FIG. 2.
Figure 4:
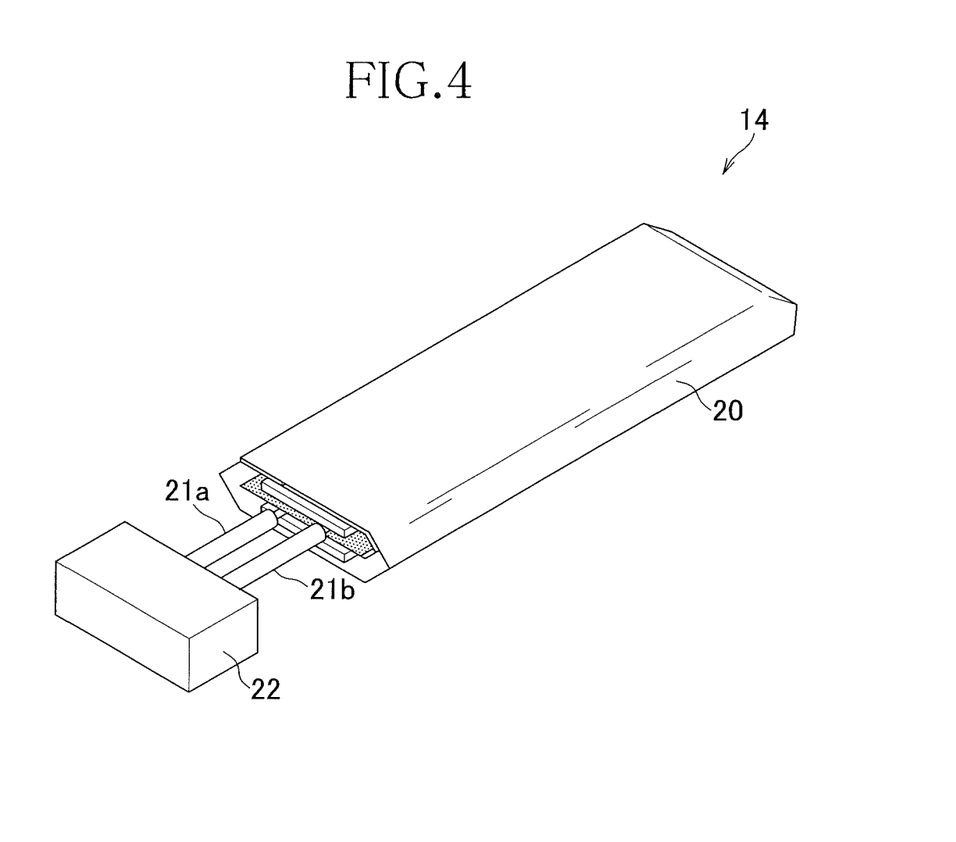
FIG. 4 is a perspective view of a sensor unit.

Referring now to FIGS. 3 and 4, the sensor unit 14 is composed of a relatively compact liquid battery 20 externally capsuled by a liquid permeable fibrous nonwoven fabric sheet and a relatively compact sender 22 coupled to the liquid battery 20 by the intermediary of lead wires 21a, 21b extending out from the liquid battery 20. The sensor unit 14 is interposed and clamped between the inner surface of the pressure-sensitive adhesive fixing tape 13 and the absorbent element 16 under the effect of an adhesive region of the pressure-sensitive adhesive fixing tape 13. The pressure-sensitive adhesive fixing tape 13 is fixed to the top H of the patient hand so as to cover almost the entire absorbent element 16 in a transverse direction of the absorbent element 16 and therefore there is no possibility that the sensor unit 14 should not be displaced during treatment. To fix the sensor unit 14 between the pressure-sensitive adhesive fixing tape 13 and the absorbent element 16 more stably and more reliably, the surface of the absorbent element 16 facing the sensor unit may be coated with an adhesive at certain interval sensuring the sensor unit 14 to be supplied with the liquid.

Referring to FIG. 3, the sensor unit 14 is placed so as to face the point 12a of the butterfly needle 12 through the intermediary of the absorbent element 16 (upper part of FIG. 3). When the liquid 26, for example, blood or infusion leaks from the blood vessel region slightly protruding due to insertion of the point 12a of the butterfly needle 12 and permeates the entire absorbent element 16 or a relatively wide range thereof around the blood vessel region, the leaked liquid 26 permeates the fibrous nonwoven fabric sheet externally capsuling the liquid battery 20. The liquid 26 permeating the fibrous nonwoven fabric sheet functions as a catalyzer causing an electrochemical reaction to develop an electromotive force within the liquid battery 20. The electromotive force generated in this manner causes electrical current to be carried via the lead wires 21a, 21b to the sender 22 which, in response to the electric current, emits electrical waves. In this way, when the liquid leakage occurs from the blood vessel region 25 in which the top 12a of the butterfly needle 12 has been pricked into the blood vessel, the sensor unit 14 located so as to face this blood vessel region 25 can quickly detect such liquid leakage and inform the persons working outside of this liquid leakage.

The electrical waves emitted from the sender 22 can be transmitted to locations remote from the leakage detection system 10 to the receivers 15 placed, for example, in a central control room such as a nurse center. Thus, for example, the receiver 15 may be directly coupled with annunciation means located in the central control room or/and a hospital to inform a plurality of persons working in the hospital of the fact that the liquid leakage has occurred, thereby preventing medical accidents due to such liquid leakage.

The liquid leakage detection system 10 according to the present invention uses, in addition to the medical components which are necessary for blood collection and drip infusion, for example, the infusion tube 11 coupled to the bag for drip infusion or blood collection, the butterfly needle 12 and the blood stanching element composed of the pressure-sensitive adhesive fixing tape 13 and the absorbent element 16, the sensor unit 14 composed of the compact liquid battery 20 and the compact sender 22 to ensure the liquid leakage to be quickly detected. Considering such aspect, it will be reasonable to evaluate the detection system according to the present invention to be more easy-to-use and more moderate in price than the conventional automatic liquid leakage detection device as well as the conventional automatic liquid leakage detection system including precision measuring equipment using semiconductor devices and integrated circuits. The side of the receiver also requires neither large scale device nor large scale system and therefore the liquid leakage detection system 10 according to the present invention can be used not only in the medical facilities such as hospitals but also in the care facilities and even for home use.

Generally, the liquid battery 20 constituting a part of the sensor unit 14 includes the electrode plate and the sender 22 is formed of a metallic element as will be described later in details. With such an arrangement, if the sensor unit comes in direct contact with the patient's skin, the patient might feel uncomfortable. However, according to the present embodiment, the sensor unit 14 is put in indirect contact with the patient skin by the intermediary of the absorbent element 16 folded in two or more layers without creating an uncomfortable feeling against the patient. Additionally, the absorbent element 16 having a required thickness is interposed between the sensor unit 14 and the patient skin and, therefore, a slight amount of liquid is retained in the absorbent element 16 before the liquid can reach the sensor unit 14. Specifically, a slight amount of blood or infusion which sometimes flows out at the moment of the needle insertion should not generate electricity and the sensor unit should not lead to a malfunctioning of the system. Furthermore, the thickness of the absorbent element and/or the number of layers of the folded absorbent element may be selected to adjust a reaction velocity from leakage of the liquid from the blood vessel to generation of electricity by the liquid battery 20 appropriately.

Figure 5:
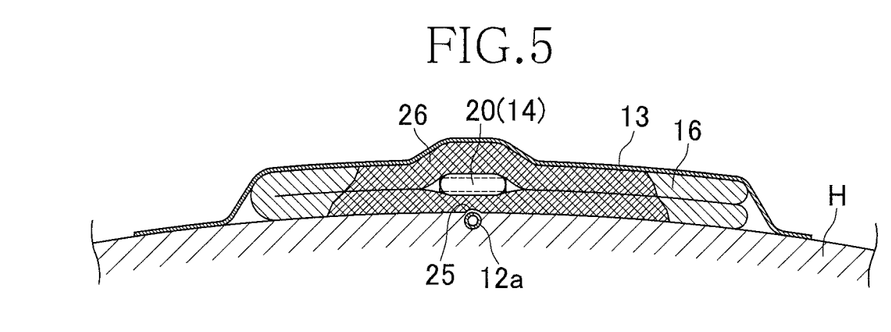
FIG. 5 is a sectional view similar to FIG. 3, illustrating another embodiment.

Referring to FIG. 5 illustrating another embodiment of the present invention, at least the liquid battery 20 constituting the sensor unit 14 may be placed so as to be interposed between upper and lower layers of the doubled up absorbent element 16. With this arrangement, the liquid battery 20 is tightly held between two layers of the doubled up absorbent element 16 and the liquid battery 20 should not be displaced during a medical treatment. In addition, the liquid battery 20 is entirely wrapped with the absorbent element 16 and consequently the liquid 26 absorbed by the absorbent element 16 and diffused therein is supplied to an entirety of the liquid battery 20. In this way, electricity generating efficiency is further improved.

So long as the liquid leakage can be detected, the liquid battery 20 may be located on the upper side of the absorbent element 16 or within the absorbent element 16 and it is not essential for the sensor unit 14 to include the sender 22. Specifically, the lead wires 21a, 21b extending from the liquid battery 20 may be directly coupled to the external annunciation means to inform the persons working in the locations remote from the detection system of the liquid leakage. Though not illustrated, it is also possible to couple the liquid battery 20 directly to the sender 22 by, for example, caulking them together without use of the lead wires 21a, 21b.

In order that such effect can be produced in the present invention, the liquid battery 20 constituting a part of the sensor unit 14 should be relatively compact and arranged so as to generate electricity as soon as the liquid battery 20 is soaked with water. Details of the arrangement of the liquid battery 20 used in the present invention to achieve the above-mentioned effect will be described hereunder.

Figure 6:
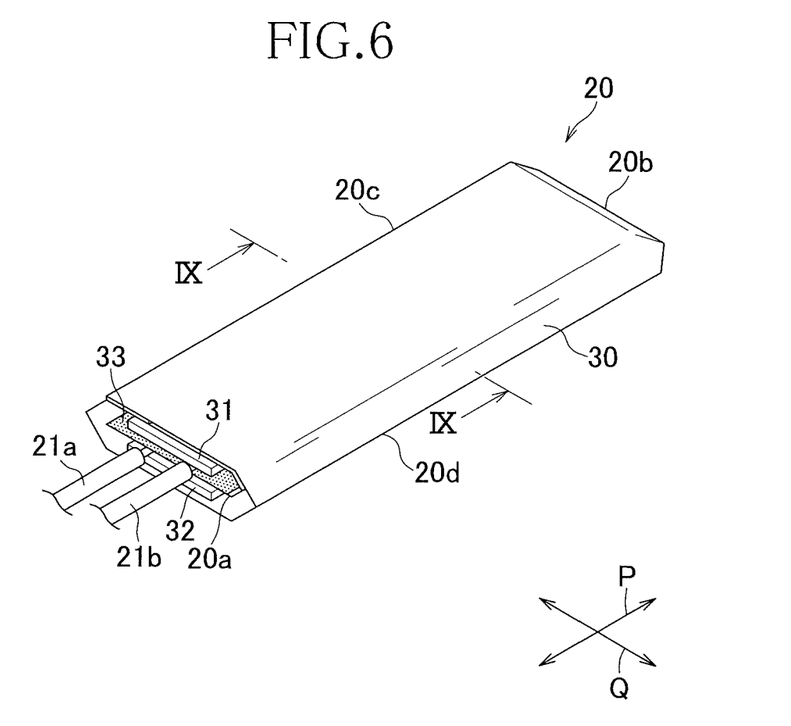
FIG. 6 is a perspective view of a liquid battery.
Figure 7:
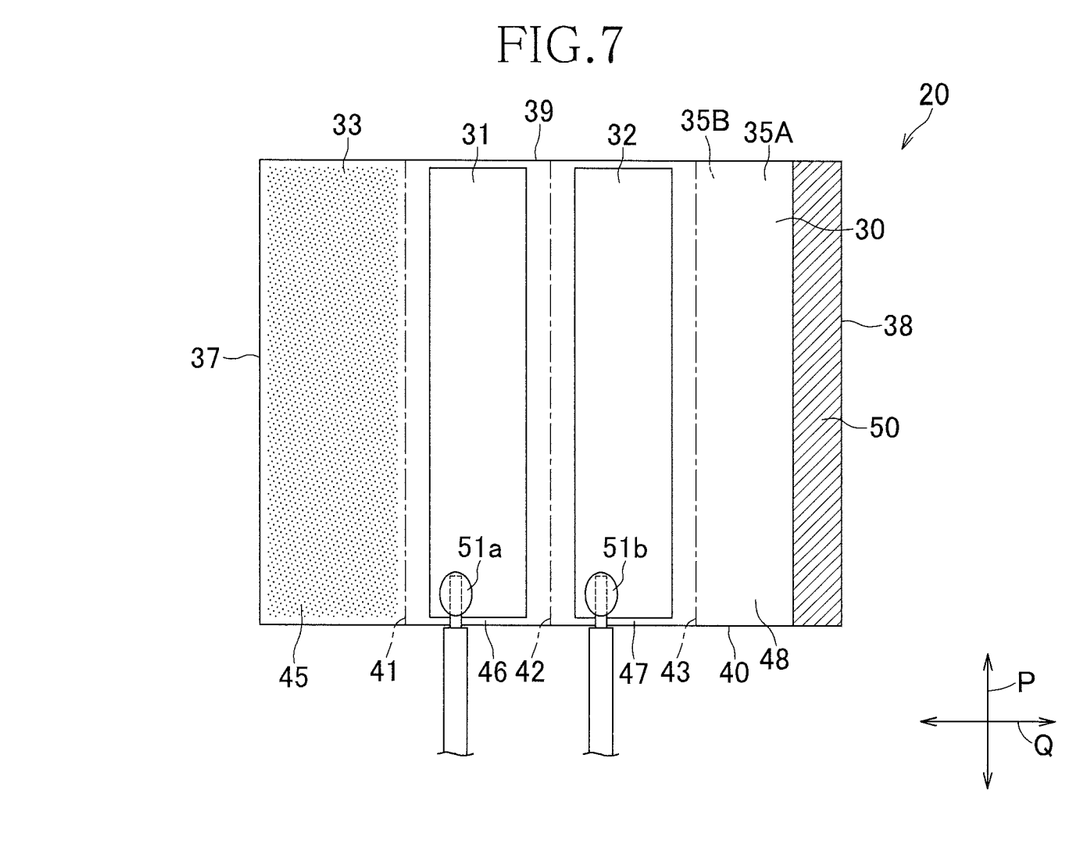
FIG. 7 is an exploded plan view of the liquid battery.
Figure 8:
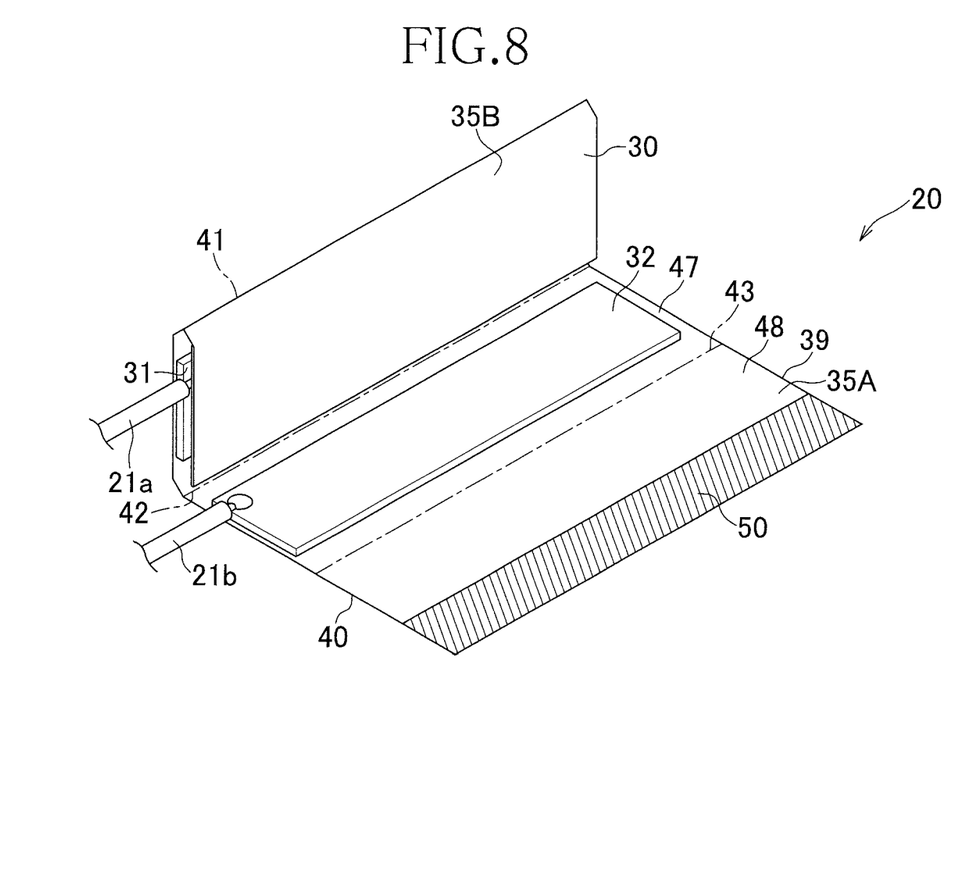
FIG. 8 is a diagram illustrating a part of an assembling process for the liquid battery.
Figure 9:
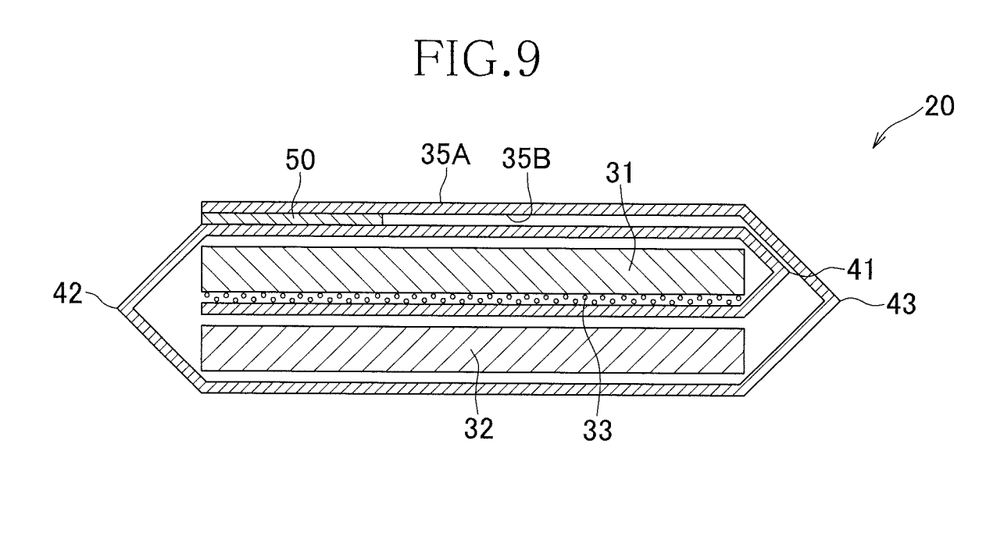
FIG. 9 is a sectional view taken along line IX-IX in FIG. 6.

FIG. 6 is a perspective view of the liquid battery 20, FIG. 7 is an exploded plan view of the liquid battery 20, FIG. 8 is a perspective view illustrating an assembling process for the liquid battery 20 and FIG. 9 is a sectional view taken along line IX-IX in FIG. 8.

The liquid battery 20 has a substantially rectangular shape defined by a longitudinal direction P, a transverse direction Q, first and second side edges 20c, 20d extending in the longitudinal direction P in parallel to each other, an open end 20a and an closed end 20b closed by adhesion or sealing and spaced apart from and opposed to the open end 20a in the longitudinal direction P. This substantially rectangular liquid battery 20 includes an external capsule sheet 30, a positive electrode plate 31, a negative electrode plate 32 both capsuled by the external capsule sheet 30, and positive-electrode active material 33 put in contact with the positive electrode plate 31 within the external capsule sheet 30. The positive electrode plate 31, the negative electrode plate 32 and the positive-electrode active material 33 are stacked on one another and capsuled by the external capsule sheet 30. The lead wires 21a, 21b attached to the positive electrode plate 31 and the negative electrode plate 32, respectively, extend outward through the open end 20a. In this regard, it is possible to close the open end 20a with an adhesive or by a heat sealing technique in a fashion similar to the closed end 20b.

The external capsule sheet 30 is made of electrically insulative and liquid-permeable sheet material, for example, a water-permeable fibrous nonwoven fabric or a porous plastic film.

As illustrated in FIG. 7, the external capsule sheet 30 has, as viewed in the developed state, a substantially square shape defined by first and second surfaces 35A, 35B, first and second side edges 37, 38 spaced apart from and opposed to each other in the transverse direction Q and extending in the longitudinal direction P, and first and second ends 39, 40 spaced apart from and opposed to each other in the longitudinal direction P and extending in the transverse direction Q wherein first-third fold lines 41, 42, 43 respectively extending in the longitudinal direction P are formed between the first and second side edges 37. 38. A width dimension of the external capsule sheet 30 in the transverse direction Q is almost evenly divided into four regions by the first and second side edges 37, 38 and the first-third fold lines 41, 42, 43. Specifically, the width dimension is divided into a first region 45 defined between the first side edge 37 and the first fold line 41, a second region 46 defined between the first fold line 41 and the second fold line 42, a third region 43 defined between the second fold line 42 and the third fold line 43 and a fourth region 48 defined between the third fold line 43 and the second side edge 38. In this regard, a joining region 50 extending in the longitudinal direction P is formed between the fourth region 48 and the second side edge 38 of the external capsule sheet 30. The joining region 50 is preferably coated with an adhesive at certain intervals to ensure that the external capsule sheet 30 may absorb water through the second surface 35B thereof and the water absorbed in this manner may function as catalyst for the oxidation reaction of the positive-electrode active material 33 placed within the external capsule sheet 30. So long as permeation of water into the liquid battery is ensured, the joining region 50 may be joined with use of a heat sealing technique instead of an adhesive. The lead wires 21a, 21b are coupled to the positive electrode plate 31 and the negative electrode plate 32 with use of soldering 51a, 51b, respectively.

The positive electrode plate 31 is a substantially rectangular thin plate placed in the second region 46 of the external capsule sheet 30 and made of material which has relatively superior electrical conductivity, indistinctive ionization tendency and relatively high electrochemical stability, for example, metals such as nickel, copper or silver, or the alloy containing such metals as principal alloy elements.

The negative electrode plate 32 is a thin plate which is substantially the same as the positive electrode plate 31 in shape as well as in size and placed in the third region 47 of the external capsule sheet 30 and made of electrode active material having relatively high ionization and/or oxidation tendencies, for example, metallic magnesium, aluminum or zinc or alloy containing at least two or more of these metals.

The positive-electrode active material 33 is powdery material bonded to the first region 45 of the external capsule sheet 30 by the intermediary of an adhesive sprayed to the first region 45 and made of oxidizing material having relatively high oxidizing power, for example, a commixture containing but not limited to activated carbon, manganese dioxide, iron oxide and crystalline silver oxide wherein kinds of the commixture and the mixing ratio for the respective commixtures are appropriately selected depending on the desired oxidizing power. In order that the liquid battery 20 as a whole can be shaped to be relatively thin and the desired electromotive force can be generated with use of a relatively small amount of the positive-electrode active material, two or more kinds of the active materials may be used or such active materials subjected to appropriate processing treatments may be used. While the positive-electrode active material 33 is powdery according to the present invention, it is also possible to form the powder of the various active materials such as the activated carbon into a sheet and to affix this sheet to the first region 45 with an adhesive. In this regard, the adhesive with which the positive-electrode active material 33 is bonded to the first region 45 is preferably applied to the sheet of the positive-electrode active material at certain intervals so that the liquid may smoothly permeate the sheet.

To transfigure the liquid battery 20 from the developed state as illustrated in FIG. 7 to the assembled state as illustrated in FIG. 6, first, as illustrated in FIG. 8, the first region 45 of the external capsule sheet 30 is folded inwardly so that the first region 45 and the second region 46 may face each other, more specifically, the positive-electrode active material 33 bonded to the first region 45 and the positive electrode plate 31 located in the second region 46 may be overlapped and put in contact with each other. Then, the regions in which the positive electrode plate 31 and the positive-electrode active material 33 are capsuled, respectively, are folded inwardly along the second fold line 42 so that the second surface 35B of the first region 45 to which the positive-electrode active material 33 is bonded and the negative electrode plate 32 located in the third region 47 may be overlapped and put in contact with each other. Finally, the fourth region 48 is folded along the third fold line 43 toward the second surface 35B of the second region 46 and the fourth region 48 is joined to the second surface 35B of the second region 46 by the intermediary of the joining region 50. In this way, the liquid battery 20 can be assembled.

Referring now to FIG. 9, within the liquid battery 20, the positive electrode plate 31 and the positive-electrode active material 33 are kept in contact with each other and the positive-electrode active material 33 is kept in contact with the negative electrode plate 32 by the intermediary of the external capsule sheet 30 to which the positive-electrode active material 33 is bonded. In the liquid battery 20 with such arrangement, when the liquid permeates the liquid battery 20 through the second surface 35B of the external capsule sheet 30 and/or the open end 20a, water is diffused in the positive-electrode active material 33 through the region defining the first region 45 of the external capsule sheet 30. The water diffused in this manner functions as catalyst for oxidation reaction and, as a result, ionization reaction develops between the both electrodes so as to generate an electromotive force.

The liquid battery 20 according to the present invention includes the respective constituent materials stacked on one another and capsuled by the external capsule sheet 30 and is, in consequence, much more thin and lightweight than the conventional cylindrical liquid battery. In addition, even when only a drop of the liquid (various kinds of liquids such as urine, water or blood) is supplied, it is possible to supply the positive-electrode active material 55 with the liquid through the external capsule sheet interposed between the respective constituent materials and to diffuse the liquid so that a required electromotive force can be quickly developed.

As for specific dimensions of the liquid battery 20, a length dimension in the longitudinal direction P of the first and second side edges 20c, 20d is in a range of about 5.0 to about 10.0 mm, a length dimension in the transverse direction Q of the open end 20a and the closed end 20b is in a range of about 2.0 to about 5.0 mm, and a thickness dimension thereof is in a range of about 0.1 to about 0.3 mm. A surface area of the positive electrode plate 31 and the negative electrode plate 32 is in a range of about 20 to about 50 $mm^2$. A mass of the positive-electrode active material 33 composed of various active materials such as activated carbon at a predetermined mixing ratio is in a range of 0.01 to 0.05 g. The liquid battery 20 dimensioned as indicated above is able to supply the sender 22 with electric current having a magnitude in a range of about 2.5 to 10.0 mA for several seconds-several minutes. In this regard, these values are exemplified for convenience of description of this embodiment and the respective dimensions of the liquid battery 20 as well as the magnitude of electrical current may be varied as the occasion demands.

Though not illustrated, it is also possible to form the liquid battery 20 including the absorbent element 16 by affixing the absorbent element 16 to a part of the external capsule sheet 30 or wedging the absorbent element 16 between parts of the external capsule sheet 30, then folding the absorbent element 16 together with the parts of the external capsule sheet 30 and fastening them with use of fastening means such as a string or a cylindrical plastic film.

Figure 10:
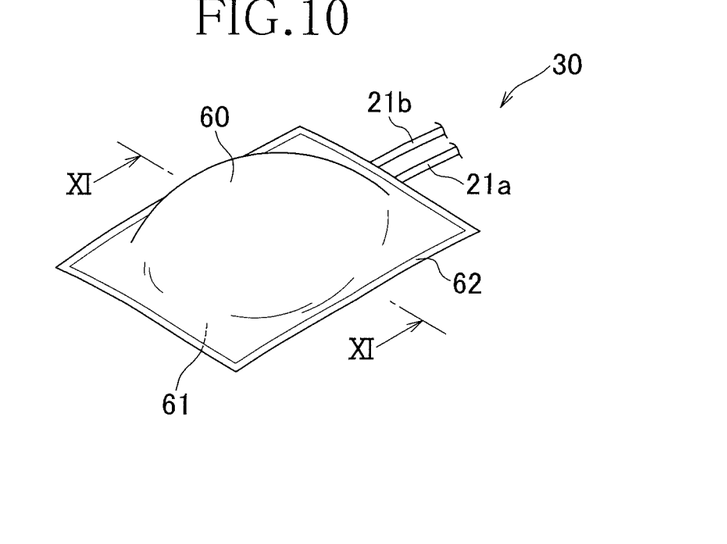
FIG. 10 is a perspective view of the sensor unit according to another embodiment.
Figure 11:
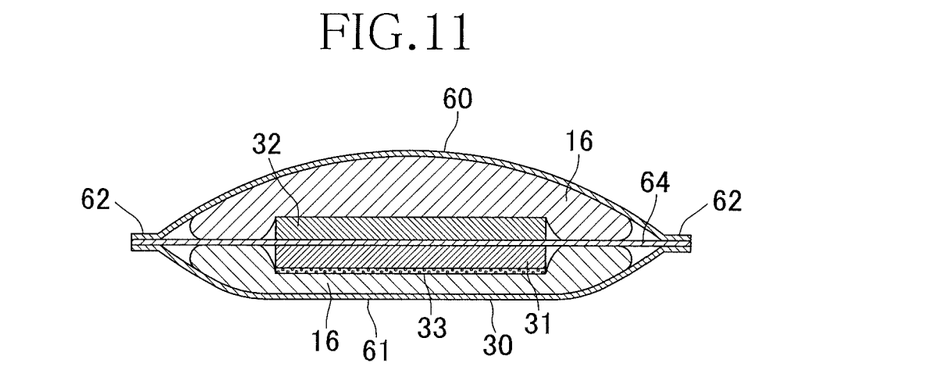
FIG. 11 is a sectional view taken along line XI-XI in FIG. 10.

FIG. 10 is a perspective view of the liquid battery 20 according to another embodiment and FIG. 11 is a sectional view taken along line XI-XI in FIG. 10. The basic arrangement of the liquid battery 20 according to the present embodiment is substantially the same as that of the liquid battery 20 illustrated in FIG. 1-FIG. 9 and therefore only the dissimilarities to the first embodiment will be described hereunder.

The liquid battery 20 according to the present embodiment has a substantially rectangular pad-like shape contoured by a first convex surface 60, a rather flat second surface 61 defined on a side opposite to the first convex surface 60, and an outer peripheral edge 62 along which the first and second surfaces 60, 61 are joined to each other by adhesion or heat sealing. The external capsule sheet 30 is formed from two substantially rectangular nonwoven fabric sheets and two absorbent elements 16 are arranged so as to be wedged between inner surfaces of the respective external capsule sheets 30. The absorbent element 16 placed on the side of the convex first surface 60 is thicker than the absorbent element 16 placed on the side of the second surface 61. A separating sheet (electrical insulator layer) 64 formed of insulative material which is the same as or different from the material of the external capsule sheet 30 is interposed between the two external capsule sheets 30 and joined to the respective external capsule sheets 30 along an outer peripheral edge 62 common to these three sheets. The lead wires 21a, 21b are secured together with these sheet members and extend outward from the liquid battery 20. While the liquid battery 20 is coupled through the lead wires 21a, 21b to the sender 22 located outside the liquid battery 20 according to the present embodiment, it is also possible to locate the sender 22 within the external capsule sheet 30 so as to form the sensor unit 14 integrally composed of the liquid battery 20 and the sender 22.

Within the external capsule sheet 30, the positive electrode plate 31 located on the side of the second surface 61 and the negative electrode plate 32 located on the side of the first surface 60 are covered with the respective absorbent elements 16 and put in indirect contact with each other by the intermediary of the separating sheet 64. Within the external capsule sheet 30, the positive-electrode active material 33 bonded to the inner surface of the absorbent element 16 by means of adhesive sprayed on the inner surface of the absorbent element 16 or formed into a sheet is kept in contact with the positive electrode plate 31.

The liquid battery 20 according to the present embodiment includes therein the absorbent element 16 and whereby it is unnecessary to interpose the absorbent element for blood stanching between the liquid battery 20 and the patient's skin. The liquid battery 20 may be positioned directly on the blood vessel region or the affected site where the point of the syringe needle is pricked to ensure blood stanching so long as an amount of bleeding is less than a predetermined amount. If leakage of liquid (e.g., blood or infusion) exceeds the predetermined amount, an electrochemical reaction will generate electromotive force within the liquid battery 20 and electric current will be carried to the sender 22 coupled to the liquid battery 20, making it possible to inform the persons working outside the system of occurrence of the liquid leakage. The second surface 61 has a rather flat shape and makes it possible to use this second surface 61 as a contact surface adapted to be stably placed on the patient's skin. The liquid battery 20 has a pad-like shape and can be put in direct contact with the patient's skin without creating an uncomfortable feeling against the patient. Such pad-like shaped liquid battery 20 is preferable also from the viewpoint of design.

REFERENCE SIGNS LIST 10 liquid leakage detection system
11 tube
12 butterfly needle (syringe needle)
13 fixing tape
14 sensor unit
16 absorbent element
20 liquid battery
22 sender
26 liquid
30 external capsule sheet
31 positive electrode plate
32 negative electrode plate
33 positive-electrode active material

The invention claimed is:

1. A liquid leakage detection system, including an infusion tube, a syringe needle coupled to the infusion tube, an absorbent element adapted to be placed in a vicinity of a point of the syringe needle to be pricked through a patient skin and a sensor unit located on an upper side or within the absorbent element, wherein the sensor unit is composed of a liquid battery adapted to generate electricity in the presence of the leaked liquid and a sender coupled to the liquid battery.

2. The detection system according to claim 1, wherein the sensor unit is provided to the absorbent element by means of a pressure-sensitive adhesive fixing tape.

3. The detection system according to claim 1, wherein the liquid battery includes a positive electrode plate, a negative electrode plate, positive-electrode active material directly or indirectly in contact with both the positive electrode plate and the negative electrode plate, and an external capsule sheet adapted to capsule them and wherein an electrical insulator layer is interposed between the positive electrode plate and the negative electrode plate.

4. The detection system according to claim 3, wherein the absorbent element is interposed between the inner surface of the external capsule sheet and the liquid battery so that the positive electrode plate and the negative electrode plate may be wrapped with the absorbent element within the external capsule sheet.

\* \* \* \* \*